United States Patent [19]

Asai et al.

[11] 4,364,866
[45] Dec. 21, 1982

[54] MAYTANSINOIDS

[75] Inventors: Mitsuko Asai, Takatsuki; Kazuo Nakahama, Muko; Motowo Izawa, Amagasaki, all of Japan

[73] Assignee: Takeda Chemical Industries, Ltd., Osaka, Japan

[21] Appl. No.: 188,238

[22] Filed: Sep. 17, 1980

[30] Foreign Application Priority Data

Sep. 21, 1979 [JP] Japan .................................. 54/122216
Nov. 20, 1979 [JP] Japan .................................. 54/150908

[51] Int. Cl.³ .................... C07D 498/16; C07D 498/18
[52] U.S. Cl. ........................ 260/239.3 P; 424/248.54; 435/119; 435/872
[58] Field of Search .............................. 260/239.3 P; 424/248.54; 260/239.3 T

[56] References Cited

PUBLICATIONS

Kupchan et al., "J. Am. Chem. Soc." vol. 42, No. 14 (1977) pp. 2349-2357.
Wani et al., "J. Chem. Soc. Communications" (1973) p. 390.

Primary Examiner—Robert T. Bond
Attorney, Agent, or Firm—Wegner & Bretschneider

[57] ABSTRACT

Antibiotic C-15003 PHO of the formula:

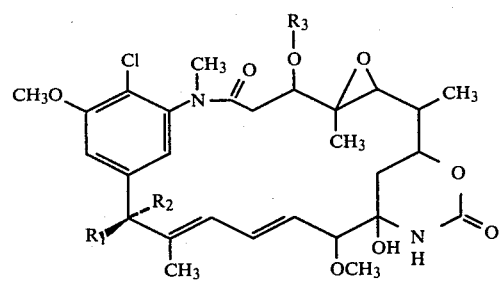

wherein $R_1$ is H, hydroxyl, alkanoyloxy, alkenylcarbonyloxy or arylcarbonyloxy; $R_2$ is H, hydroxyl or alkanoyloxy; $R_3$ is H or alkanoyloxy is produced by introducing a hydroxyl group into 15-position of a maytansinoid compound, and, if desired, thus obtained compound is subjected to deacylation or acylation.

Antibiotic C-15003 PHO is useful as antiprotozoal or antitumor agent.

20 Claims, No Drawings

MAYTANSINOIDS

This invention relates to Antibiotic C-15003 PHO and the production thereof.

The research undertaken by the present inventors to develop a method for microbiological transformation of a maytansinoid compound into other compounds led to the discovery that a hydroxyl group could be introduced into the 15-position of a certain maytansinoid compound by permitting a culture of a certain microorganism or a processed matter derived therefrom to act upon said maytansinoid compound and that a compound having a hydroxyl group in 3-position could be obtained by deacylating the resulting compound. And the present inventors also discovered that the acyl derivatives obtained by acylation of said compounds have excellent biological activity and conducted further studies on the above finding. This invention has been accomplished on the strength of the above findings and studies.

This invention is concerned with:

(1) A maytansinoid compound (I) of the formula:

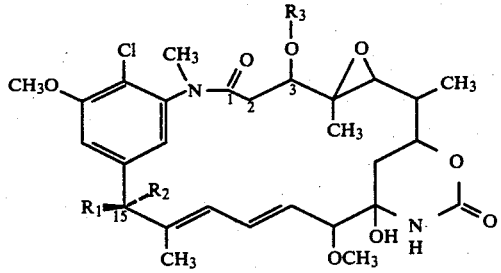

wherein
$R_3$ means H or alkanoyl containing not more than 5 carbon atoms except

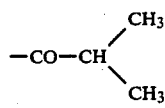

when $R_1$ is OH and $R_2$ is H; $R_3$ means H or alkanoyl containing not more than 5 carbon atoms when $R_1$ is H and $R_2$ is OH;

when $R_3$ means H or alkanoyl of 2 to 5 carbon atoms other than

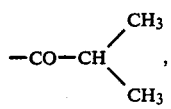

$R_1$ is formyloxy, alkanoyloxy of 2 to 7 carbon atoms, alkenylcarbonyloxy of 3 to 5 carbon atoms or arylcarbonyloxy, which may optionally be substituted, and $R_2$ is H;

when $R_3$ means

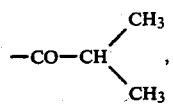

$R_1$ is formyloxy, alkanoyloxy of 3 to 7 carbon atoms, alkenylcarbonyloxy of 3 to 5 carbon atoms or arylcarbonyloxy, which may optionally be substituted, or substituted acetoxy and $R_2$ is H;

or $R_3$ means H or alkanoyl containing not more than 5 carbon atoms when $R_1$ is H and $R_2$ is alkanoyloxy of 2 to 5 carbon atoms, and (2) A method of producing a maytansinoid compound (I') of the formula:

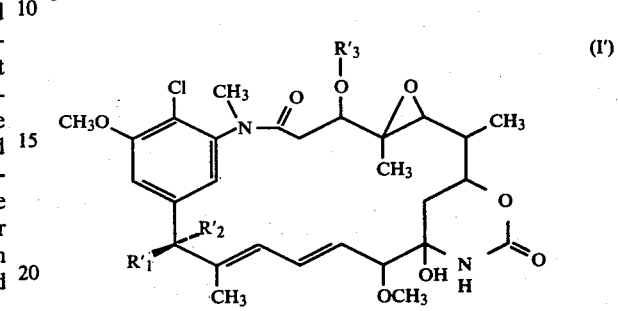

wherein $R_1'$ is H, hydroxyl, formyloxy, alkanoyloxy of 2 to 7 carbon atoms, alkenylcarbonyloxy of 3 to 5 carbon atoms or arylcarbonyloxy, which may optionally be substituted; $R_2'$ is H, hydroxyl or alkanoyloxy of 2 to 5 carbon atoms; $R_3'$ is H or alkanoyl containing not more than 5 carbon atoms characterized by contacting a maytansinoid compound (II) of the formula:

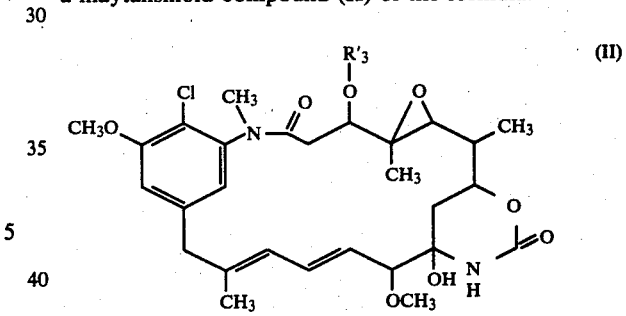

wherein $R_3'$ is as defined above with a culture, or a processed matter derived therefrom, of a microorganism belonging to one of the genera Streptomyces, Chainia and Streptosporangium and capable of introducing a hydroxyl group into the 15-position of the compound (II), and, if desired, thus obtained compound (III) of the formula:

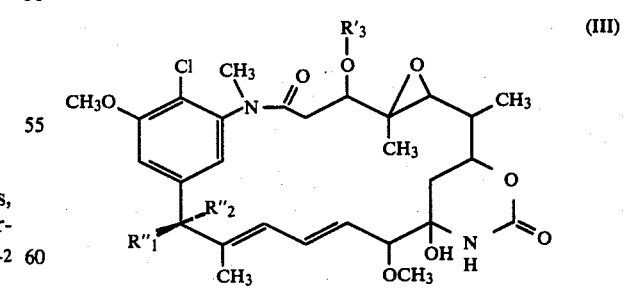

wherein $R_1''$ is H or hydroxyl, $R_2''$ is H or hydroxyl, and $R_3'$ is as defined above is subjected to deacylation, and further, if desired, the above-obtained compound (III) is subjected to acylation.

Referring to the above general formulas, the alkanoyl group of not more than 5 carbon atoms may for example be formyl (—CHO), acetyl (—COCH₃), propionyl (—COCH₂CH₃), butyryl (—COCH₂CH₂CH₃), isobutyryl

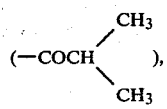

valeryl (—COCH₂CH₂CH₂CH₃), isovaleryl

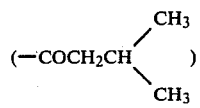

or the like.

The alkyl group in the alkanoyloxy (=alkylcarbonyloxy) of 2 to 7 carbon atoms may be straight or branched and includes methyl, ethyl, n-propyl, isopropyl, n-butyl, isobutyl, sec-butyl, tert-butyl, pentyl, isopentyl, 1-methylpropyl, hexyl, isohexyl etc. The alkyl group in the alkanoyloxy (=alkylcarbonyloxy) of 3 to 7 carbon atoms may be straight or branched. Examples are such ones as mentioned above for the alkyl other than methyl. Examples of the alkyl group in the alkanoyloxy (=alkylcarbonyloxy) of 2 to 5 carbon atoms are methyl, ethyl, n-propyl, isopropyl, n-butyl, isobutyl, sec-butyl and tert-butyl.

The alkenyl group in the alkenylcarbonyloxy of 3 to 5 carbon atoms is, for example, vinyl, allyl, 1-methylvinyl or 2-methylvinyl.

The aryl group in the arylcarbonyloxy includes phenyl, benzyl, cinnamyl, phenethyl, styryl, etc.

The above-mentioned alkyl, alkenyl and aryl may be substituted by at most three substituents which may be the same or different. Examples of the substituents are C₁–C₄ alkoxy (e.g. methoxy, ethoxy, propoxy, isopropoxy, n-butoxy, iso-butoxy, sec-butoxy, tert-butoxy), C₂–C₄ alkanoyl (e.g. acetyl, propionyl, n-butyryl, iso-butyryl), C₂–C₄ alkanoyloxy (e.g. acetyloxy, propionyloxy, n-butyryloxy, isobutyryloxy), C₂–C₄ alkoxycarbonyl (e.g. methoxycarbonyl ethoxycarbonyl, n-propoxycarbonyl, iso-propoxycarbonyl), halogen (e.g. chlorine, fluorine, bromine, iodine), nitro, cyano, trifluoromethyl, di-C₁₋₄-alkylamino (e.g. dimethylamino, diethylamino, dipropylamino, diisopropylamino, dibutylamino), C₁–C₄ alkylthio (e.g. methylthio, ethylthio, n-propylthio, isopropylthio, n-butylthio, isobutylthio, sec-butylthio, tert-butylthio), methylsulfinyl, methylsulfonyl, oxo, thioxo, C₁–C₄ alkanoylamido (e.g. formamido, acetamido, propionylamido, butyrylamido, isobutyrylamido) and carboxyl. The aryl mentioned above may be substituted by C₁–C₄ alkyl (e.g. methyl, ethyl, n-propyl, iso-propyl, n-butyl, iso-butyl, sec-butyl, tert-butyl). Examples of the substituents of the substituted acetoxy are the same as mentioned above.

Examples of the substituted alkyl group in the substituted alkanoyloxy of 2 to 7 carbon atoms are methoxymethyl, butoxymethyl, methylthiomethyl, methylthioethyl, ethylthioethyl, isopropylthioethyl, butylthioethyl, isobutylthioethyl, acetyloxymethyl, acetyloxyethyl, ethoxycarbonylmethyl, ethoxycarbonylethyl, butoxycarbonylethyl, fluoromethyl, chloromethyl, chloroethyl, 3-chloropropyl, 4-chlorobutyl, 3,3,3-trichloropropyl, trifluoromethyl, bromomethyl, 4-bromobutyl, 5-bromopentyl, iodomethyl, 2-iodoethyl, 1,1-dimethyl-2,2-dichloroethyl, 2-chloro-1-chloromethyl-1-methylethyl, cyanomethyl, methylsulfinylethyl, methylsulfonylmethyl, carboxymethyl and carboxyethyl.

Examples of the substituted alkyl group in the substituted alkanoyloxy of 3 to 7 carbon atoms are methoxyethyl, butoxyethyl, methylthioethyl, methylthioethyl, ethylthioethyl, isopropylthioethyl, butylthioethyl, isobutylthioethyl, acetyloxyethyl, ethoxycarbonylethyl, butoxycarbonylethyl, fluoroethyl, chloroethyl, 3-chloropropyl, 4-chlorobutyl, 3,3,3-trichloropropyl, 4-bromobutyl, 5-bromopentyl, 2-iodoethyl, 1,1-dimethyl-2,2-dichloroethyl, 2-chloro-1-chloromethyl-1-methylethyl, cyanoethyl, methylsulfinylethyl, 2-methylsulfonylethyl and carboxyethyl.

The substituted alkenyl group in the substituted alkenylcarbonyloxy of 3 to 5 carbon atoms is, for example, 1-chlorovinyl.

Examples of the substituted aryl group in the substituted arylcarbonyloxy are 2-, 3- or 4-methylphenyl, 4-tert-butylphenyl, 2-, 3- or 4-chlorophenyl, 2-, 3- or 4-bromophenyl, 2-, 3- or 4-iodophenyl, 2-, 3- or 4-fluorophenyl, 2- or 4-methoxyphenyl, 4-butoxyphenyl, 4-methoxycarbonylphenyl, 3-acetylphenyl, 2-, 3- or 4-nitrophenyl, 3- or 4-cyanophenyl, 4-dimethylaminophenyl, 4-diethylaminophenyl, 4-acetoxyphenyl, 4-butyryloxyphenyl, 2,4-, 2,5-, 2,6-, 3,4- or 3,5-dichlorophenyl, 3,4-dimethoxyphenyl, 3,4,5-trimethoxyphenyl, 3,4-methylenedioxyphenyl, 3-trifluoromethylphenyl, 4-methylthiophenyl, 4-methylsulfonylphenyl and 4-acetamidophenyl.

The term "C-15003 PHO" or, simply, "PHO" as used throughout this specification means all of the compounds of the formula (I) wherein R₁ is OH and R₂ is H, its derivatives, a mixture of two or more of such compounds or any one of the compounds. Among the compounds of general formula (I), the compound (I) wherein R₁ is OH, R₂ is H and R₃ is H will be referred to as "C-15003 PHO-0" or briefly as "PHO-0"; the compound (I) wherein R₁ and R₂ are as defined above and R₃ is —COCH₃ will be referred to as "C-15003 PHO-1" or briefly as "PHO-1"; the compound (I) wherein R₁ and R₂ are as defined above and R₃ is —COCH₂CH₃ will be referred to as "C-15003 PHO-2" or briefly as "PHO-2"; the compound (I') wherein R₁' is OH, R₂' is H and R₃' is

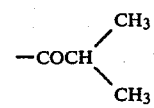

will be referred to as "C-15003 PHO-3" or briefly as "PHO-3"; and the compound (I) wherein R₁ and R₂ are as defined above and R₃ is

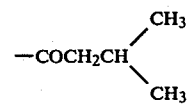

will be referred to as "C-15003 PHO-4" or briefly as "PHO-4".

The term "C-15003 epi-PHO" means all of the compounds of general formula (I) wherein R₁ is H and R₂ is OH, its derivative a mixture of two or more of such compounds or any one of the same compounds. The compounds of general formula (I) wherein R₁ is H, R₂ is OH and R₃ is H will hereinafter be referred to as "C-15003 epi-PHO-0" or briefly as "epi-PHO-0"; the compound (I) wherein R₁ and R₂ are as defined above and R₃ is —COCH₃ will hereinafter be referred to as "C-15003 epi-PHO-1" or briefly as "epi-PHO-1"; the compound (I) wherein R₁ and R₂ are as defined above and R₃ is —COCH₂CH₃ will be referred to as "C-15003 epi-PHO-2" or briefly as "epi-PHO-2"; the compound (I) wherein R₁ and R₂ are as defined above and R₃ is

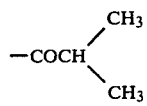

will be referred to as "C-15003 epi-PHO-3" or briefly as "epi-PHO-3"; and the compound (I) wherein R₁ and R₂ are as defined above and R₃ is

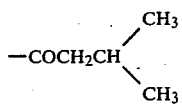

will be referred to as "C-15003 epi-PHO-4" or briefly as "epi-PHO-4".

The compound of general formula (II) wherein R₃' is H, i.e. maytansinol, will hereinafter be referred to as "P-0"; the compound (II) wherein R₃' is —COCH₃, i.e. maytanacine, will be referred to as "P-1"; the compound (II) wherein R₃' is —COCH₂CH₃, i.e. maytansinol propionate, will be referred to as "P-2"; the compound (II) wherein R₃' is

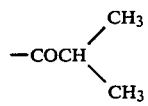

will be referred to as "C-15003 P-3" or briefly as "P-3"; the compound (II) wherein R₃' is —COCH₂CH₂CH₃ will be referred to as "C-15003 P-3'" or briefly as "P-3'"; and the compound (II) wherein R₃' is

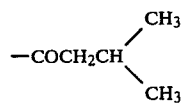

will be referred to as "C-15003 P-4" or briefly as "P-4".

P-0, P-1, P-2, P-3, P-3' and P-4 can be obtained by cultivating a microorganism, for example Nocardia sp. No. C-15003 [deposited at Fermentation Research Institute, Agency of Industrial Science and Technology, Japan under the number of FERM-P No. 3992; Institute for Fermentation, Osaka, Japan under the number of IFO 13726; and The American Type Culture Collection, U.S.A. under the number of ATCC 31281], in a culture medium and harvesting and purifying them from the fermentation broth [Nature vol. 270, p. 721 (1977), Tetrahedron 35, 1079 (1979), U.S. Pat. No. 4,151,042, U.S. Pat. No. 4,162,940]. The straim ATCC 31281 is listed on "The American Type Culture Collection Catalogue of Strains I(Fourteenth edition 1980)".

P-0 can also be obtained by deacylating P-3, P-3' and/or P-4 [Nature, vol. 270, p.721 (1977), Tetrahedron 35, 1079 (1979), U.S. Pat. No. 4,162,940].

The compounds of general formula (II) wherein R₃' is alkanoyl containing not more than 5 carbon atoms can be produced by reacting P-0 with an acid anhydride of general formula:

[wherein R₄ is alkanoyl containing not more than 5 carbon atoms] derived from the corresponding carboxylic acid or with an acid halide of general formula:

$$R_4X \quad (VII)$$

[wherein R₄ is as defined above; X is halogen] which is also derived from the corresponding carboxylic acid.

Referring to the above general formula (VII), the halogen X may for example be chlorine, bromine or iodine.

There are cases in which the above reaction is preferably carried out in the presence of a base. As examples of the base may be mentioned tertiary amines such as triethylamine, tributylamine, pyridine, 4-dimethylaminopyridine, α-, β- or γ-picoline, 2,6-lutidine, dimethylaniline, diethylaniline, N-methylmorpholine, etc. Also, the above reaction may be conducted in an appropriate solvent which may for example be esters (e.g. ethyl acetate), ethers (e.g. diethyl ether, dioxane, tetrahydrofuran), halogenated hydrocarbons (e.g. methylene chloride, chloroform), nitriles (e.g. acetonitrile), aromatic hydrocarbons (e.g. benzene), nitromethane, dimethylformamide, dimethyl sulfoxide, sulfolane, etc. as well as mixture of such solvents. It is also possible to employ the above-mentioned base as the solvent or a mixture of the base with the solvent mentioned above. While the reaction temperature is not particularly critical, the reaction is desirably carried out at −20° C. to +40° C. The resulting compound of general formula (II) wherein R₃' is alkanoyl containing not more than 5 carbon atoms can be purified by routine separation and purification procedures such as solvent extraction, chromatography, recrystallization, etc.

The microorganism employed in the method of the reaction from the compound (II) to the compound (III) may be any organism belonging to one of the genera Streptomyces, Chainia and Streptosporangium which is capable of introducing a hydroxyl group into the 15-position of the compound (II), inclusive of variants and mutants thereof. Thus, as examples of organisms which can be employed in the practice of this invention there may be mentioned *Streptomyces sclerotialus* IFO 12246 (ATCC 15721), *Streptomyces castaneus* IFO 13670, *Streptomyces flavochromogenes* IFO 13443 (ATCC 14841), *Streptomyces olivaceiscleroticus* IFO 13484 (ATCC 15722), *Streptomyces flaviscleroticus* IFO 13357 (ATCC 19347), *Chainia nigra* IFO 13362 (ATCC 17756) and *Streptosporangium roseum* IFO 3776.

The above-mentioned strains are listed on "Institute for Fermentation Osaka List of Cultures (1978 sixth edition)", and the strains referred with ATCC numbers are listed on "The American Type Culture Collection Catalogue of Strains I (Thirteenth Edition 1978)".

Generally, organisms of the genera Streptomyces, Chainia and Streptosporangium are highly variable in characteristics and can be mutated by artificial means such as X-ray, UV, gamma-ray or other irradiation, or with a mutagenic agent (e.g. nitrosoguanidine, ethyleneimine, etc.). Even such mutants can also be employed for the purposes of this invention only if they are still able to introduce a hydroxyl group into the 15-position of maytansinoid compound (II).

The medium used for the cultivation of said microorganism in the method according to this invention may be a liquid medium or a solid medium, when it contains sources of nutrients which said microorganism can utilize, although a liquid medium is preferred for high production runs. In the medium are incorporated the carbon sources which said organism can assimilate, the nitrogen sources which it can digest, inorganic substances, trace nutrients and so forth in suitable proportions. The carbon sources may include, among others, glucose, lactose, sucrose, maltose, dextrin, starch, glycerol, mannitol, sorbitol, etc., oils and fats (e.g. soybean oil, lard oil, chicken oil, etc.), etc. The nitrogen sources may include, among others, meat extract, yeast extract, dried yeast, soybean flour, corn steep liquor, peptone, cottonseed oil, spent molases, urea, ammonium salts (e.g. ammonium sulfate, ammonium chloride, ammonium nitrate, ammonium acetate, etc.) and the like. In addition, use may also be made of salts of sodium, potassium, calcium, magnesium, etc., metal salts such as salts of iron, manganese, zinc, cobalt, nickel, etc; salts of phosphoric acid, boric acid, etc.; and salts of organic acids such as salts of acetic acid, propionic acid, etc. It is further possible to incorporate amino acids (e.g. glutamic acid, aspartic acid, alanine, glycine, lysine, methionine, proline, etc.), peptides (e.g. dipeptides, tripeptides, etc.), vitamins (e.g. $B_1$, $B_2$, nicotinic acid, $B_{12}$, C, E, etc.), nucleic acids (e.g. purine, pyrimidine and their derivatives) and so forth. Of course, it is possible to add inorganic or organic acids, alkalis, buffers, etc. for the purpose of adjusting the pH of medium or to add a suitable amount of fats and oils, surfactants, etc. for defoaming purposes.

The cultivation method may be stationary culture, shake culture or aerated stirring culture. For high production runs, the so-called submerged aerobic culture is of course desirable. While cultivation conditions depend upon the condition and composition of medium, the particular strain of organism, cultural method employed and so forth, generally the cultivation is desirably carried out at a temperature in the range of 20° C. to 45° C. and at an initial pH level of near neutral. It is especially desirable to maintain the temperature at 24° C. to 37° C. at intermediate stages of cultivation and start the cultivation at a pH of 6.5 to 8.5. The cultivation time may range from 6 to 100 hours and the range of 16 to 48 hours is particularly desirable.

The term "culture broth" as used in this specification means the broth obtained by the above-described cultivation procedure.

The term "processed matter" means the mycelial or cellular products obtained from said culture broth by a physical or/and chemical treatments, e.g. filtration, centrifugation, supersonication, French-pressing, grinding with alumina, bacteriolytic enzyme treatment, treatment with a surfactant or organic solvent, etc. or a equivalent milled product containing a hydroxylase. It is also possible to employ the corresponding hydroxylase obtained by a conventional purification procedure or the mycelial or cellular product or hydroxylase immobilized by a conventional procedure.

The method of this invention is carried into practice by contacting the starting compound (II) with the culture broth or processed matter as obtained or derived from the above-mentioned microorganism. The concentration of said starting compound (II) in the reaction system is preferably in the range of 1 to 500 µg/ml. The reaction temperature and pH are desirably 20° to 50° C. and pH 5 to 10, and more desirably about 24° to 40° C. and pH 6 to 9. The reaction time is 1 to 200 hours and, more desirably 24 to 72 hours. The reaction may be conducted under stationary, shake, aerated or stirring conditions, although shake, aerated or stirring conditions are preferred.

The product obtainable in the above manner can be detected by thin-layer chromatography (TLC hereinafter). Thus, the reaction mixture is extracted with ethyl acetate, concentrated to one-hundredth by volume and subjected to TLC on a silica gel glass plate (E. Merck, Germany, silicagel $60F_{254}$, 0.25 mm, 20×20 cm) with a solvent system of chloroform and methanol (9:1). The zone absorbing in ultraviolet light at 2537 Å is scraped off to obtain the desired fraction.

Since the product substance group is neutral lipophilic, the desired compound can be isolated from the reaction system by means of the isolation and purification procedures commonly used in the recovery of microbial metabolites. Such procedures are exemplified by procedures utilizing differences in solubility with respect to impurities, procedures utilizing differences in adsorptive affinity for various adsorbents such as activated carbon, macroporous nonionic resin, silica gel, alumina, etc., and procedures for removing impurities with ion exchange resins, and these procedures may be used either independently, in combination or in repetition. The suitable solvent for use in procedures utilizing a solubility difference include, for example, fatty acid esters (e.g. ethyl acetate, amyl acetate, etc.), alcohols (e.g. butanol, etc.), halogenated hydrocarbons (e.g. chloroform, etc.), and ketones (e.g. methyl isobutyl ketone, etc.). The extraction is carried out near neutral pH and a preferred procedure comprises adjusting the broth filtrate to pH 7 and extracting it with ethyl acetate. The extract is then washed with water and concentrated under reduced pressure, and a nonpolar solvent such as petroleum ether or hexane is added. The crude product (i) containing active substances is thus obtained. Since the TLC of this crude product gives many spots other than the desired compound (III), the following stepwise purification process is applied. Thus, as routine methods, various adsorption chromatographic techniques can be successfully utilized. While the adsorbents may be those commonly employed, e.g. silica gel, alumina, macroporous nonionic adsorbent resin, etc., silica gel is most effective for purification from crude product (i). The adsorbent column is developed first with, for example, petroleum ether or/and n-hexane and, then, with the addition of a polar solvent or solvent system such as ethyl acetate, acetone, ethanol or/and methanol, whereby the desired compound (III) are eluted. As an example, column chromatography on silica gel (E. Merck, Germany, 0.05–0.2 mm) is carried out and the chromatogram is developed with sequential increases in the ratio of ethyl acetate to n-hexane. The eluate is scanned by TLC and the fractions containing the compound (III) are combined, concentrated under reduced pressure and treated with petroleum ether or n-hexane to recover a crude product (ii). If this product still contains much impurities, it is further purified. By way of example, such additional purification can be performed on second silica gel column with a different solvent system. As to the developing solvents, the column is developed first with a halogenated hydrocarbon such as dichloromethane, chloroform, etc. and then with addition of a polar solvent or solvent system such as alcohol (e.g. ethanol, methanol, etc.) or/and ketone (e.g. acetone, methyl ethyl ketone, etc.), whereby the desired compound (III) is isolated. The solvents for said first and second silica gel columns may be reversed or identical. It is also possible to use other common organic solvents in various combinations.

When the resulting crude product (iii) contains the compound (III) wherein $R_1$ is H and $R_2$ is OH in addition to the compound (III) wherein $R_1$ is OH and $R_2$ is H, it is further subjected to the following purification procedure. Thus, the above-mentioned adsorption chromatographic techniques and partition chromatographic techniques can be utilized with advantage, but to further purify the crude product (iii), reverse phase partition gel chromatography is very useful. The eluent may be a water-miscible alcohol or ketone solvent. As an example, preparative separation is carried out by high performance liquid chromatography, i.e. Prep IC/system 500 (Waters Associates Inc., U.S.A.) on reverse-phase gel $C_{18}$ (Water Associates Inc., U.S.A., Prep PAK-500/$C_{18}$). When aqueous methanol is used as the solvent, the compound (III) wherein $R_1$ is H and $R_2$ is OH and the compound (III) wherein $R_1$ is OH and $R_2$ is H emerge in that order. After detection by reverse-phase TLC (E. Merck, Germany), the fraction of the compound (III) wherein $R_1$ is H and $R_2$ is OH and the fraction of the compound (III) wherein $R_1$ is OH and $R_2$ is H are respectively concentrated under reduced pressure. Each concentrate is extracted with ethyl acetate, concentrated under reduced pressure and, after addition of a small amount of methanol, allowed to stand, whereupon colorless crystals of the corresponding compounds are obtained.

The compound (III) can be used also as intermediate for the synthesis of pharmaceutically useful compounds. Thus, by deacylating the compound (III), there can be obtained a compound of the formula (IV) having a hydroxyl group in the 3-position.

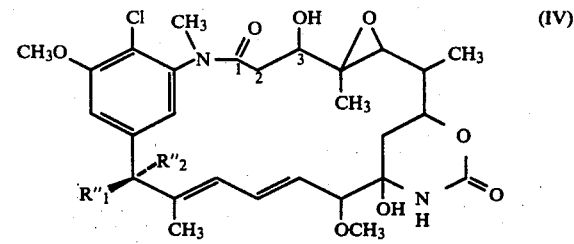

$R''_1$ and $R''_2$ are as defined above.

In this case, because the acyl group is in the position beta to the carbonyl group, the conventional reductive hydrolysis reaction can be employed with advantage. Thus, by using a metal hydride complex compound [e.g. lithium aluminum hydride (LiAlH$_4$)] at a low temperature (e.g. $-20°$ C. to $0°$ C.), the O-ester bond in 3-position can be hydrolyzed without affecting other functional groups, e.g. the carbonyl, epoxy, carbon-carbon double bond, etc., so as to yield a compound (IV) of the formula (IV). The isolation and purification of the compound (IV) can be performed in the same manner as described hereinbefore.

Tables 1 and 2 show the physico-chemical properties of PHO-0 as obtained in Example 5, PHO-1 as obtained in Example 7, PHO-2 as obtained in Example 9, PHO-3 as obtained in Example 3, PHO-4 as obtained in Example 11, epi-PHO-0 as obtained in Example 5, epi-PHO-1 as obtained in Example 7, epi-PHO-2 as obtained in Example 9, epi-PHO-3 as obtained in Example 3 and epi-PHO-4 as obtained in Example 11, all of said Examples appearing hereinafter.

TABLE 1

| | C—15003 PHO | | |
|---|---|---|---|
| | PHO—0 | PHO—1 | PHO—2 |
| Mol. formula & mol. wt. | $C_{28}H_{37}ClN_2O_9$ =581.079 | $C_{30}H_{39}ClN_2O_{10}$ =623.115 | $C_{31}H_{41}ClN_2O_{10}$ =637.141 |
| $[\alpha]_D^{23}$, ethanol | $-178° \pm 10°$ (c = 0.4) | $-102° \pm 10°$ (c = 0.14) | $-107° \pm 10°$ (c = 0.22) |
| Mass spectrum (m/e) | 519, 501, 483, 474 468, 448 | 561, 543, 508. 501 483, 468, 448 | 575, 557, 522, 501 483, 468, 448 |
| Ultraviolet absorption spectrum nm($\epsilon$) MeOH | 233 (29600) 252 (25700) 281 ( 4990) 289 ( 4990) | 233 (27000) 252 (23500) 281 ( 4560) 289 ( 4560) | 233 (26800) 252 (23300) 281 ( 4550) 289 ( 4550) |
| Infrared absorption spectrum (cm$^{-1}$) (KBr) | 1704, 1663, 1080 | 1740, 1704, 1663, 1238, 1080 | 1740, 1704, 1663, 1080 |
| Nuclear magnetic resonance spectrum (ppm, 90MHz) | 5.27 (1H,s) 6.98(1H,d) 7.36(1H,d) etc. (deuterio-chloroform + deuterio-acetone) | 5.37 (1H,s) 6.88(1H,d) 7.49(1H,d) etc. (deuterio-acetone) | 5.37(1H,s) 6.86(1H,d) 7.49(1H,d) etc. (deuterio-acetone) |
| Solubility | Pyridine, dimethylformamide, dimethyl sulfoxide: readily soluble. Tetrahydrofuran, acetone, methanol, chloroform, ethyl acetate: soluble. n-Hexane, petroleum ether: insoluble. | Pyridine, dimethylformamide, dimethyl sulfoxide readily soluble. Tetrahydrofuran, acetone, methanol, chloroform, ethyl acetate: soluble. n-Hexane, petroleum ether: insoluble. | Pyridine, dimethylformamide, dimethyl sulfoxide: readily soluble. Tetrahydrofuran, acetone, methanol, chloroform, ethyl acetate: soluble. n-Hexane, petroleum ether: insoluble. |
| Color reaction | Dragendorff: | Dragendorff: | Dragendorff: |

TABLE 1-continued

|  | positive<br>Beilstein:<br>negative | positive<br>Beilstein:<br>negative | positive<br>Beilstein:<br>negative |
|---|---|---|---|
| Thin-layer chromatography<br>Silica gel glass plate |  |  |  |
| (a) Chloroform-methanol<br>(9:1) | (a) 0.19 | (a) 0.32 | (a) 0.36 |
| (b) $H_2O$-saturated ethyl<br>acetate | (b) 0.10 | (b) 0.16 | (b) 0.23 |
| Reverse phase gel<br>glass plate |  |  |  |
| (c) 80% aqueous methanol | (c) 0.66 | (c) 0.68 | (c) 0.66 |

|  | C—15003 PHO | |
|---|---|---|
|  | PHO—3 | PHO—4 |
| Mol. formula & mol. wt. | $C_{32}H_{43}ClN_2O_{10}$<br>=651.167 | $C_{33}H_{45}ClN_2O_{10}$<br>=665.193 |
| $[\alpha]_D^{23}$, ethanol | $-96° \pm 10°$<br>(c = 0.515) | $-108° \pm 10°$<br>(c = 0.50) |
| Mass spectrum (m/e) | 589, 571, 536, 501<br>483, 468, 448 | 603, 585, 550, 501<br>483, 468, 448 |
| Ultraviolet absorption spectrum<br>nm($\epsilon$)<br>MeOH | 233 (26600)<br>252 (23100)<br>281 ( 4520)<br>289 ( 4520) | 233 (26300)<br>252 (22900)<br>281 ( 4500)<br>289 ( 4500) |
| Infrared absorption spectrum<br>($cm^{-1}$)<br>(KBr) | 1740, 1704,<br>1663, 1080 | 1740, 1704,<br>1663, 1080 |
| Nuclear magnetic resonance<br>spectrum<br>(ppm, 90MHz) | 5.37(1H,s)<br>6.90(1H,d)<br>7.49(1H,d)<br>etc.<br>(deuterio-acetone) | 5,37(1H,s)<br>6.88(1H,d)<br>7.49(1H,d)<br>etc.<br>(deuterio-acetone) |
| Solubility | Pyridine, dimethylformamide,<br>dimethyl sulfoxide: readily<br>soluble.<br>Tetrahydrofuran, acetone<br>methanol, chloroform, ethyl<br>acetate: soluble.<br>n-Hexane, petroleum ether:<br>insoluble. | Pyridine, dimethylformamide,<br>dimethyl sulfoxide: readily<br>soluble.<br>Tetrahydrofuran, acetone<br>methanol, chloroform, ethyl<br>acetate: soluble,<br>n-Hexane, petroleum ether:<br>insoluble. |
| Color reaction | Dragendorff: positive<br>Beilstein: negative | Dragendorff: positive<br>Beilstein: negative |
| Thin-layer chromatography<br>Silica gel glass plate |  |  |
| (a) Chloroform-methanol<br>(9:1) | (a) 0.38 | (a) 0.40 |
| (b) $H_2O$-saturated ethyl<br>acetate Reverse<br>phase gel glass plate | (b) 0.26 | (b) 0.29 |
| (c) 80% aqueous methanol | (c) 0.64 | (c) 0.62 |

TABLE 2

|  | C—15003epi-PHO | | |
|---|---|---|---|
|  | epi-PHO—0 | epi-PHO—1 | epi-PHO—2 |
| Mol. formula & mol. wt. | $C_{28}H_{37}ClN_2O_9$<br>= 581.079 | $C_{30}H_{39}ClN_2O_{10}$<br>= 623.115 | $C_{31}H_{41}ClN_2O_{10}$<br>= 637.141 |
| $[\alpha]_D^{23}$, ethanol | $-208° \pm 10°$<br>(c = 0.32) | $-130° \pm 10°$<br>(c = 0.14) | $-128° \pm 10°$<br>(c = 0.26) |
| Mass spectrum (m/e) | 519,501,483,474<br>468,448 | 561,543,508,501<br>483,468,448 | 575,557,522,501<br>483,468,448 |
| Ultraviolet absorption spectrum<br>nm($\epsilon$)<br>MeOH | 233 (29600)<br>253 (26700)<br>281 ( 5490)<br>289 ( 5490) | 233 (28500)<br>253 (25800)<br>281 ( 5280)<br>288 ( 5280) | 233 (28300)<br>253 (25500)<br>281 ( 5240)<br>288 ( 5240) |
| Infrared absorption spectrum<br>($cm^{-1}$)<br>(KBr) | 1703, 1660,<br>1090 | 1740, 1703,<br>1660, 1239,<br>1090 | 1740, 1703,<br>1660, 1090 |
| Nuclear magnetic resonance<br>spectrum<br>(ppm, 90MHz)<br>(deuterio-acetone) | 5.11(1H,s)<br><br><br>etc. | 5.11(1H,s)<br>7.22(1H,d)<br>7.26(1H,d)<br>etc. | 5.11(1H,s)<br>7.22(1H,d)<br>7.27(1H,d)<br>etc. |
| Solubility | Pyridine,<br>dimethylformamide,<br>dimethyl sulfoxide:<br>readily soluble.<br>Tetrahydrofuran,<br>acetone, methanol, | Pyridine,<br>dimethylformamide,<br>dimethyl sulfoxide:<br>readily soluble.<br>Tetrahydrofuran,<br>acetone, methanol, | Pyridine,<br>dimethylformamide,<br>dimethyl sulfoxide:<br>readily soluble.<br>Tetrahydrofuran,<br>acetone, methanol, |

TABLE 2-continued

| | | | |
|---|---|---|---|
| Color reaction | chloroform, ethyl acetate: soluble. n-Hexane, petroleum ether: insoluble. Dragendorff: positive Beilstein: negative | chloroform, ethyl acetate: soluble. n-Hexane, petroleum ether: insoluble. Dragendorff: positive Beilstein: negative | chloroform, ethyl acetate: soluble. n-Hexane, petroleum ether: insoluble. Dragendorff: positive Beilstein: negative |
| Thin-layer chromatography Silica gel glass plate | | | |
| (a) Chloroform-methanol (9:1) | (a) 0.18 | (a) 0.31 | (a) 0.35 |
| (b) H$_2$O-saturated ethyl acetate | (b) 0.10 | (b) 0.15 | (b) 0.22 |
| Reverse phase gel glass plate | | | |
| (c) 80% aqueous methanol | (c) 0.70 | (c) 0.72 | (c) 0.70 |

| | C—15003epi-PHO | |
|---|---|---|
| | epi-PHO—3 | epi-PHO—4 |
| Mol. formula & mol. wt. | C$_{32}$H$_{43}$ClN$_2$O$_{10}$ = 651.167 | C$_{33}$H$_{45}$ClN$_2$O$_{10}$ = 665.193 |
| $[\alpha]_D^{23}$, ethanol | $-123° \pm 10°$ (c = 0.47) | $-131° \pm 10°$ (c = 0.46) |
| Mass spectrum (m/e) | 589,571,536,501 483,468,448 | 603,585,550,501 483,468,448 |
| Ultraviolet absorption spectrum nm($\epsilon$) MeOH | 233 (28100) 253 (25400) 281 ( 5220) 289 ( 5220) | 233 (27800) 253 (25100) 281 ( 5160) 289 ( 5160) |
| Infrared absorption spectrum (cm$^{-1}$) (KBr) | 1740, 1703, 1660, 1090 | 1740, 1703, 1660, 1090 |
| Nuclear magnetic resonance spectrum (ppm, 90MHz) (deuterio-acetone) | 5.11(1H,s) 7.20(1H,d) 7.27(1H,d) etc. | 5.11(1H,s) 7.21(1H,d) 7.27(1H,d) etc. |
| Solubility | Pyridine, dimethylformamide, dimethyl sulfoxide: readily soluble. Tetrahydrofuran, acetone, methanol, chloroform, ethyl acetate: soluble. n-Hexane, petroleum ether: insoluble. | Pyridine, dimethylformamide, dimethyl sulfoxide: readily soluble. Tetrahydrofuran, acetone, methanol, chloroform, ethyl acetate: soluble. n-Hexane, petroleum ether: insoluble. |
| Color reaction | Dragendorff: positive Beilstein: negative | Dragendorff: positive Beilstein: negative |
| Thin-layer chromatography Silica gel glass plate | | |
| (a) Chloroform-methanol (9:1) | (a) 0.37 | (a) 0.39 |
| (b) H$_2$O-saturated ethyl acetate | (b) 0.25 | (b) 0.28 |
| Reverse phase gel glass plate | | |
| (c) 80% aqueous methanol | (c) 0.68 | (c) 0.66 |

Comparison of the above physico-chemical properties with the properties of the known maytansinoid compounds has shown that the properties of PHO-3 are in good agreement with those of deactylmaytanbutacine as described in the Journal of Organic Chemistry 42, 2349 (1977). Further, when PHO-3 is acetylated, the product compound showed physico-chemical properties in good agreement with those described for maytanbutacine in the above-mentioned literature. However, there was no compound corresponding to any other compound (III). Therefore, epi-PHO-3 will now be compared with PHO-3. Since the same fragment is detected in mass spectra, it is easy to presume that like PHO-3, epi-PHO-3 is a compound formed on the introduction of hydroxyl group into PHO. In nuclear magnetic resonance spectrum, a singlet assignable to the 15-hydrogen atom is found at $\delta$5.37 for PHO-3 and at $\delta$5.11 for epi-PHO-3. This fact suggests that epi-PHO-3 is a stereo-isomer at 15-position of PHO-3 and, therefore, that epi-PHO-3 is a novel compound. Furthermore, X-ray analysis has shown that the absolute configuration of C$_{15}$ of epi-PHO-3 is S-configuration. Comparison of the other compounds (III) with PHO-3 and epi-PHO-3 indicates that the structural formulas of these compounds are as shown in formulas 1 and 2, respectively.

Formula 1

-continued

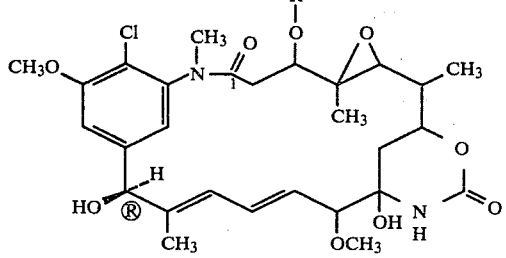

| PHO | R |
|---|---|
| PHO—0 | H |
| PHO—1 | —CO—CH$_3$ |
| PHO—2 | —CO—CH$_2$—CH$_3$ |
| PHO—3 | —CO—CH(CH$_3$)$_2$ |
| PHO—4 | —CO—CH$_2$—CH(CH$_3$)$_2$ |

Formula 2

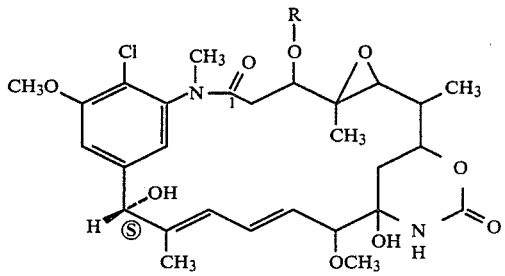

| epi-PHO | R |
|---|---|
| epi-PHO—0 | H |
| epi-PHO—1 | —CO—CH$_3$ |
| epi-PHO—2 | —CO—CH$_2$—CH$_3$ |
| epi-PHO—3 | —CO—CH(CH$_3$)$_2$ |
| epi-PHO—4 | —CO—CH$_2$—CH(CH$_3$)$_2$ |

P-0 (maytansinol) which is obtainable by reductive cleavage reaction of P-1, P-2, P-3, P-3′ or P-4 is identical with maytansinol which is the nucleus of maytansine [Nature 270, 721–722 (1977), Tetrahedron 35, 1079–1085 (1979)] and as mentioned hereinbefore, P-0, P-1 and P-2 respectively correspond to maytansinol, maytanacine and maytansinol propionate which are described in Journal of the American Chemical Society 97, 5294 (1975). Therefore, the absolute configuration of asymmetric carbon atoms $C_3$, $C_4$, $C_5$, $C_6$, $C_7$, $C_9$ and $C_{10}$ contained in P-0 (maytansinol) are the same as those of maytansine as reported in Journal of the American Chemical Society 94, 1354–1356 (1972). Thus, the absolute configurations of such asymmetric carbon atoms in the compound (III) are all the same as the above and the data from the above-mentioned X-ray analysis of the compound (III) wherein $R_1$ is H and $R_2$ is OH indicate also that the configurations are 3S, 4S, 5S, 6R, 7S, 9S and 10R.

Maytanbutacine which is obtainable by acetylating C-15003 PHO-3 with acetic anhydride in the per se conventional manner [the Journal of Organic Chemistry 42, 2349 (1977)] has been shown to have antitumor activity as mentioned in Journal of Medicinal Chemistry 21, 31 (1978). Thus, the compounds (III) are valuable intermediates in the production of various derivative compounds. According to the published literature, maytanbutacine from plants is available only from limited varieties of plants and its production from such plants involves a great deal of cost, equipment and time for the stages of cultivation and felling of plants, drying, pulverization, and extraction and purification of the compound. Moreover, its yield is very low. In contrast, this invention enables one to produce its precursor PHO-3 by means of a microorganism with expedience, at desired times and in quantities.

The compounds (III), which can thus be produced in accordance with this invention, have antitumor and antiprotozoal activities. The antimicrobial activity of these compounds will be described below.

Using trypticase-soy-agar (Baltimore Biologicals, U.S.A.) as a test medium, the minimal inhibitory concentrations of each compound against the following microorganisms were determined by the paper disk method. Thus, on plate media containing the following organisms, growth inhibition was investigated using paper disks (Toyo Roshi Corp., Japan, thin-type, diam. 8 mm) imbibed with 0.02 ml of a 300 μg/ml solution of PHO-3 or epi-PHO-3. The study showed that these compounds did not exhibit activity against the following microorganisms:

*Escherichia coli, Proteus vulgaris, Proteus mirabilis, Pseudomonas aeruginosa, Staphylococcus aureus, Bacillus subtitis, Bacillus cereus, Klebsiella pneumoniae, Serratia marcescens, Mycobacterium avium.*

On the other hand, *Tetrahymena pyriformis* W strain, as a test organism, was cultivated on an assay medium [Proteose-peptone (Difco) 20 g, yeast extract 1 g, glucose 2 g, distilled water 1000 ml, 1 M phosphate buffer (pH 7.0) 10 ml] at 28° C. for 44 hours and the minimal inhibitory concentrations of the antibiotics against said organism were determined by the serial broth dilution method. It was thus found that PHO-3 and epi-PHO-3 inhibit growth of the above organism at the concentrations of 16 to 32 μg/ml and 16 to 32 μg/ml, respectively.

Therefore, the compound (III) can be used as antiprotozoal agents. As an antiprotozoal agent, the compound (III) can be advantageously used as a testing agent for the assay of bacterial ecology in a soil, activated sludge, animal fluid or other sample. Thus, for the purpose of separating useful bacteria from soil samples or for testing the actions of bacteria to the exclusion of protozoas in the operation and analysis of an active sludge system used in the treatment of waste water, the above compounds can be utilized to permit selective growth of bacterial life without allowing concomitant protosoas in the specimen to grow. An exemplary specific procedure comprises adding the specimen to a liquid or solid medium, adding 0.1 ml of a 1% aqueous solution of methanol containing 1000 μg/ml of the compound (III) to each ml of the medium and incubating the mixture.

It should also be noted that the compound (III) shows an increased solubility behavior in water.

The compound (III), which can be obtained by the method of this invention, can be acylated at the 15-OH function to give a 15-acyl compound which has antitumor and antiprotozoal activities. Therefore, the compound (III) is useful as an intermediate for the production of a medicine. And the compound (IV) is also useful as an intermediate for the production of a useful compound.

The acylation reaction can be accomplished for example by reacting the compound (III) with a carboxylic acid (VIII) of the formula:

$$R_5-OH \qquad (VIII)$$

wherein $R_5$ is formyl or alkanoyl of 2 to 7 carbon atoms, alkenylcarbonyl of 3 to 5 carbon atoms or arylcarbonyl, which may optionally be substituted or a reactive derivative of carboxyl group thereof.

An exemplary acylation procedure comprises acylating the compound (III) with said carboxylic acid (VIII) in the presence of a carbodiimide.

Based on starting compound (III), the carboxylic acid (VIII) may be used in a proportion of about 1 to 500 molar equivalents, preferably about 1 to 30 molar equivalents.

Based on starting compounds (III), said carbodiimide may be used in a proportion of about 1 to 700 molar equivalents and, preferably, about 1 to 50 equivalents. The carbodiimide that can be employed is any compound containing a carbodiimide bond (—N=C=N—) which is convertible to a urea bond in the course of reaction, and may for example be a compound of the following formula:

$$R_6-N=C=N-R_7 \qquad (IX)$$

[wherein $R_6$ and $R_7$ each means an organic residue conductive to a convertion of the carbodiimide bond into a urea bond in the present acylation reaction].

As examples of organic residues $R_6$ and $R_7$ there may be mentioned $C_{3-7}$ cycloalkyl groups which may optionally have di-lower ($C_{1-6}$; the same applies hereinafter) alkyl amino; lower alkyl groups which may optionally have di-lower alkylamino or morpholino, and phenyl groups which may optionally have lower alkyl. The carbodiimide preferred for commercial production is dicyclohexylcarbodiimide, although use may also be made of diphenylcarbodiimide, di-o-tolylcarbodiimide, di-p-tolylcarbodiimide, di-tert-butylcarbodiimide, 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide, 1-ethyl-3-(3-dimethylaminopropyl)carbodiimide, etc.

This acylation reaction may be carried out in an appropriate solvent, such as esters (e.g. ethyl acetate), ethers (e.g. diethyl ether, dioxane, tetrahydrofuran), halogenated hydrocarbons (e.g. methylene chloride, chloroform), nitriles (e.g. acetonitrile), aromatic hydrocarbons (e.g. benzene), nitromethane, pyridine, dimethylformamide, dimethylformamide, dimethyl sulfoxide, sulfolane, etc. inclusive of suitable mixtures of such solvents.

The acylation reaction may be carried out at a suitable temperature, usually from ice-cooling up to the reflux temperature of the reaction system.

The acylation reaction proceeds with further advantage in the presence of a catalyst assisting in acylation. Thus, for example, a basic catalyst or an acid catalyst may be utilized. The basic catalyst is exemplified by tertiary amines [such as aliphatic tertiary amines, e.g. triethylamine; and aromatic tertiary amines, e.g. pyridine, α-, β- or γ-picoline, 2,6-lutidine, 4-dimethylaminopyridine, 4-(1-pyrrolidinyl)pyridine, dimethylaniline, diethylaniline], alkali metal halides (e.g. potassium fluoride, lithium iodide anhydrate), organic acid salts (e.g. sodium acetate) and so on. The acid catalyst is exemplified by Lewis acids [e.g. zinc chloride anhydrate aluminum chloride anhydrate ($AlCl_3$), tin tetrachloride ($SnCl_4$), antimony pentachloride, cobalt chloride, cupric chloride, boron trifluoride etherate], inorganic strong acids (e.g. sulfuric acid, perchloric acid, hydrogen chloride, hydrogen bromide), organic strong acids (e.g. benzenesulfonic acid, p-toluenesulfonic acid, trifluoroacetic acid, trichloroacetic acid), acidic ion exchange resin (e.g. polystyrenesulfonic acid), etc. Among the above catalysts, 4-dimethylaminopyridine, 4-(1-pyrrolidinyl)pyridine, etc. are preferred.

The catalyst may be used in a catalytic amount i.e. an amount sufficient to promote the acylation of the compound (III) with carboxylic acid (VIII), i.e. usually from about 0.001 to 10 molar equivalents and preferably from about 0.01 to 1 molar equivalent based on compound (VIII). In many instances, the use of such a catalyst causes a substantial increase in the yield of the objective compound. It also helps realize savings in the amount of carboxylic acid (VIII); for example, to reduce the amount of (VIII) to about 1 to 10 molar equivalents relative to starting compound (III).

The acylation reaction using a reactive derivative of carboxyl group of carboxylic acid (VIII) may for example be an acylation with a derivative having a functional group capable of acylating the 15-hydroxyl group of starting compound (III), such as an acid anhydride or acid halide (e.g. chloride, bromide), of carboxylic acid (VIII). The solvent and catalyst for this acylation procedure may be those mentioned for acylation in the presence of a carbodiimide reagent. The reaction temperature may usually range from about −40° C. to +100° C., preferably about −20° C. to +40° C., although further heating may be applied in order to increase the reaction rate.

The compound produced in the above acylation can be isolated from the reaction mixture by the known procedure such as concentration, extraction with a solvent, chromatography, recrystallization, etc. With the above acylation, a compound (V) is produced.

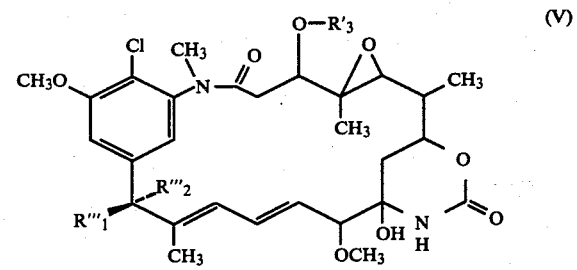

wherein
$R_1'''$ is H, formyloxy, alkanoyloxy of 2 to 7 carbon atoms, alkenylcarbonyloxy of 3 to 5 carbon atoms or arylcarbonyloxy, which may optionally be substituted;
$R_2'''$ is H or alkanoyloxy of 2 to 5 carbon atoms;
$R_3'$ is as defined above.

The compound (V) which can thus be produced in accordance with this invention have antitumor and antiprotozoal activities. The antimicrobial activity of these compounds will be described below.

Using trypticase-soy-agar (Baltimore Biologicals, U.S.A.) as a test medium, the minimal inhibitory concentrations of each compound against the following microorganisms were determined by the paper disk method. Thus, on plate media containing the following organisms, growth inhibition was investigated using paper disks (Toyo Roshi Corp., Japan, thin-type, diam. 8 mm) imbibed with 0.02 ml of a 300 µg/ml solution of PHO-3 15-valerate or epi-PHO-3 15-acetate. The study showed that these compound did not exhibit activity against the following microorganisms:

*Escherichia coli, Proteus vulgaris, Proteus mirabilis, Pseudomonas aeruginosa, Staphylococcus aureus, Bacilus subtilis, Bacillus cereus, Klebsiella pneumoniae, Serratia marcescens, Mycobacterium avium.*

On the other hand, *Tetrahymena pyriformis* W strain, as a test organism, was cultivated on an assay medium [Proteose-peptone (Difco) 20 g, yeast extract 1 g, glucose 2 g, distilled water 1000 ml, 1 M phosphate buffer (pH 7.0) 10 ml] at 28° C. for 44 to 48 hours and the minimal inhibitory concentrations of the antibiotics against said organism were determined by the serial broth dilution method. The minimal inhibitory concentrations were as follows. PHO-3 15-n-valerate: 4 µg/ml, PHO-3 15-formate: 32 µg/ml, PHO-3 15-propionate: 8 µg/ml, PHO-3 15-n-butyrate: 4 µg/ml, PHO-3 15-benzoate: 8–16 µg/ml, PHO-3 15-succinate: 32 µg/ml, PHO-3 15-ethylsuccinate: 4–8 µg/ml, PHO-3 15-monochloroacetate: 8 µg/ml, PHO-3 15-acrylate: 4–8 µg/ml, PHO-3 15-crotonate: 2 µg/ml, PHO-3 15-i-valerate: 4 µg/ml, PHO-3 15-i-butyrate: 4 µg/ml, PHO-0 15-n-valerate: >16 µg/ml, epi-PHO-3 15-acetate: 8–16 µg/ml.

Compounds (V) have antiprotozoal activity and can therefore be used as antiprotozoal agents. As an antiprotozoal agent, each of these compounds can be advantageously used as a testing agent for the assay of bacterial ecology in a soil, activated sludge, animal fluid or other sample. Thus, for the purpose of separating useful bacteria from soil samples or for testing the actions of bacteria to the exclusion of protozoas in the operation and analysis of an active sludge system used in the treatment of waste water, the above compounds can be utilized to permit selective growth of bacterial life without allowing concomitant protozoa in the specimen to grow. An exemplary specific procedure comprises adding the specimen to a liquid or solid medium, then adding 0.1 ml of a 1% aqueous solution of methanol containing 100–500 µg/ml of said compound to each ml of the medium and incubating the mixture.

Because compounds (V) prolong the survival times of warm-blooded animals (e.g. mouse, rat, dog, cat, etc.), these compounds can be used as antitumor drugs.

As an antitumor drug, each compound (V) can be administered parenterally or orally. Among parenteral routes, injection is preferred. Thus, compound (V) may be administered subcutaneously, intraperitoneally, intravenously or intramuscularly, for instance. The dosage may range from about 12.5 to 1000 µg/kg body weight/one dose, for instance, and be varied with reference to condition, animals species, etc. Such an injection can be prepared in the conventional manner. Thus, for example, about 100 µg to 3000 µg of the compound (V) of this invention is dissolved in about 0.5 ml of alcohol (e.g. methanol, ethanol), followed by addition of physiological saline to make a total of 10 ml. When the dose is small, the solution can be diluted with physiological saline.

And toxicity of the compound (V) is low.

The following Reference Examples and Examples are further illustrative of the present invention. The percent means weight/volume percent otherwise indicated.

REFERENCE EXAMPLE 1

In 1.0 ml of dichloromethane was dissolved 23.5 mg of P-0 and at about 22° C., 70.5 mg (about 10 mol equivalents) of acetic-formic anhydride (prepared by cooling 2 ml of acetic anhydride to −5° C. to 0° C., adding 1 ml of 99% formic acid thereto under stirring at −5° C. to 0° C. over a period of about 10 minutes, heating the mixture at 50° C. for 15 minutes and quenching it to 0° C.) and 11.7 mg of 4-dimethylaminopyridine. The mixture was stirred at room temperature (about 22° C.) overnight. Then, 10 drops of methanol were added to the reaction mixture and after stirring at room temperature for 3 hours, the reaction mixture was concentrated to dryness under reduced pressure. The residue was spotted on a silica gel preparative thin-layer chromatographic plate and developed twice with $H_2O$-saturated ethyl acetate. The silica gel at about 6.0 to 8.0 cm from the base line was scraped off and extracted with 10% methanol-dichloromethane. The solvent was then distilled off under reduced pressure to obtain maytansinol formate [compound (II) where $R_3'$=CHO] as a colorless glass-like substance.

REFERENCE EXAMPLE 2

The procedure of Reference Example 1 was applied to P-0 and valeric anhydride to obtain maytansinol 3-n-valerate [compound (II) where $R_3'$=—$COCH_2CH_2CH_2CH_3$], m.p. 165°–168° C.

EXAMPLE 1

*Streptomyces sclerotialus* IFO 12246 was inoculated into a medium (pH 7.5) containing 2% dextrin, 0.5% peptone, 0.5% yeast extract and 0.5% meat extract, and cultivation was carried out under shaking at 28° C. for 16 hours. To 20 l of the resulting culture was added 4 g of P-3 and the reaction was carried out under shaking at 28° C. for 48 hours. Thin-layer chromatography of this reaction broth showed that P-3 had decreased in amount and, instead, PHO-3 and epi-PHO-3 had been produced.

EXAMPLE 2

To 22 l of the reaction broth obtained in Example 1 were added 2.2 kg of sodium chloride and 11 l of ethyl acetate, and extraction was carried out under stirring. This procedure was repeated twice. The ethyl acetate layers were combined and washed with 6 l of 1/200 N hydrochloric acid, twice with 6 l portions of 1/10 M aqueous sodium carbonate and twice with 6 l portions of water. The solution was dried over anhydrous sodium sulfate and concentrated under reduced pressure, followed by addition of petroleum ether, whereupon 2.34 g of crude product (i) was obtained. This crude product (i) (2.34 g) was dissolved in a small amount of chloroform and applied to the top of a column containing 200 ml of silica gel (E. Merck, Germany, 0.063–0.2 mm). Then, 200 ml of chloroform, 300 ml of chloroform-methanol (50:1) and 300 ml of chloroform-methanol (25:1) were passed through the column and the eluate was collected in 10 ml fractions. Each fraction was spotted on a silica gel glass plate (Merck, Germany, silicagel 60F$_{254}$, 0.25 mm, 20×20 cm) and developed with chloroform-methanol (9:1). The fractions absorbing in ultraviolet light (2537 Å) were investigated and the fractions Nos. 55 through 72 at R$_f$ 0.37 to 0.38 were collected and concentrated under reduced pressure to a volume of about 10 ml. The above procedure provided 1.4 g of crude product (ii). This crude product (ii) (1.4 g) was dissolved in a small amount of warm ethyl acetate and the solution was allowed to stand at room temperature. By this procedure were obtained 1.309 g of mixed crystals of PHO-3 and epi-PHO-3.

EXAMPLE 3

In 2 ml of methanol were dissolved 300 mg of the mixed crystals obtained in Example 2 and the solution was subjected to preparative high performance chromatography using Prep LC/System 500 (Waters Associates Inc., U.S.A.). Using a reverse phase column (Waters Associates Inc., U.S.A., Prep PAK-500/C$_{18}$, 5.7 cm×30 cm), 55% aqueous methanol as the solvent was passed at the flow rate of 50 ml/min. and the fraction (Fraction A) emerging during the period of 20 to 25 minutes from the start of elution was recovered. The fraction from 25 to 35 minutes was recycled and the fraction from 35 to 47 minutes (Fraction B) was recovered. Then, the fraction from 55 to 73 minutes (Fraction C) was recovered. The fraction from 73 to 77 minutes (Fraction W) and the fraction from 77 to 93 minutes (Fraction D) were recovered. A 10 ml portion of each recovered fraction was concentrated to dryness, and ater 0.1 ml of methanol was added, the residue was spotted on a reverse phase gel glass plate (E. Merck, Germany, RP-18F$_{254}$, 10×10 cm). After development with 80% aqueous methanol, detection was carried out with ultraviolet light (2537 Å). The Fraction A and C absorbing at Rf 0.68 were combined and the Fractions B and D absorbing at Rf 0.64 were combined. Each mixture was concentrated under reduced pressure to remove the methanol. Each of the concentrates was extracted twice with 200 ml portions of ethyl acetate. Each ethyl acetate solution was dried over anhydrous sodium sulfate, concentrated under reduced pressure and allowed to stand. The above procedure yielded crystals of epi-PHO-3 (52 mg) from Fractions A and C and crystals of PHO-3 (134 mg) from Fractions B and D.

EXAMPLE 4

To 5 l of the culture broth of *Streptomyces screlotialus* IFO 12246 prepared in Example 1 was added 1 g of P-0 and the reaction was carried out under shaking at 28° C. for 48 hours. TLC of this reaction broth showed that P-0 had decreased in amount and, instead, PHO-0 and epi-PHO-0 had been produced.

EXAMPLE 5

The reaction broth obtained in Example 4 was subjected to purification procedure in the manner as Examples 2 and 3 to obtain epi-PHO-0 (37 mg) and PHO-0 (128 mg).

EXAMPLE 6

To 5 l of the culture broth of *Streptomyces sclerotialus* IFO 12246 was added 1 g of P-1 and the reaction was carried out under shaking at 28° C. for 48 hours. TLC of this reaction broth showed that P-1 had decreased in amount and instead, PHO-1 and epi-PHO-1 had been produced.

EXAMPLE 7

The reaction broth obtained in Example 6 was subjected to purification procedure in the manner as Examples 2 and 3 to obtain epi-PHO-1 (41 mg) and PHO-1 (114 mg).

EXAMPLE 8

To 5 l of the culture of *Streptomyces sclerotialus* IFO 12246 obtained in Example 1 was added 1 g of P-2 and the reaction was carried out under shaking at 28° C. for 48 hours. TLC of this reaction broth showed that P-2 had decreased in amount and, instead, PHO-2 and epi-PHO-2 had been produced.

EXAMPLE 9

The reaction broth obtained in Example 8 was subjected to purification procedure in the manner as Examples 2 and 3 to obtain epi-PHO-2 (22 mg) and PHO-2 (108 mg).

EXAMPLE 10

To 5 l of the culture broth of *Streptomyces sclerotialus* IFO 12246 was added 1 g of P-4 and the reaction was carried out under shaking at 28° C. for 48 hours. TLC of the reaction broth showed that P-4 had decreased and instead PHO-4 and epi-PHO-4 had been produced.

EXAMPLE 11

The reaction broth obtained in Example 10 was subjected to purification procedure in the manner as Examples 2 and 3 to obtain epi-PHO-4 (43 mg) and PHO-4 (134 mg).

EXAMPLE 12

*Streptomyces castaneus* IFO 13670 was inoculated into 10 l of a medium (pH 7.2) containing 1% dextrin, 1% glucose, 1% glycerol, 0.5% peptone, 0.5% yeast extract, 0.5% meat extract, 0.3% sodium chloride and 0.5% precipitated calcium carbonate. At the same time, 1 g of P-3 was added and the reaction was carried out under shaking at 28° C. for 96 hours. TLC of this reaction broth showed that P-3 had decreased in amount and, instead PHO-3 had been produced.

EXAMPLE 13

The reaction broth (10 l) obtained in Example 12 was subjected to purification procedure in the manner as Example 2 to obtain crystals of PHO-3 (670 mg). Reverse-phase gel thin-layer chromatography (glass plate: Kieselgel 60F$_{254}$, 0.25 mm, 20×20 cm; developing solvent: chloroform-methanol (9:1) of these crystals reveals a single spot at Rf 0.64.

EXAMPLE 14

A mutant strain of *Streptomyces castaneus* IFO 13670 was inoculated into 5 l of a midium (pH 7.2) containing 1% dextrin, 1% glucose, 1% glycerol, 0.5% peptone, 0.5% yeast extract, 0.5% meat extract, 0.3% sodium chloride and 0.5% precipitated calcium carbonate, and at the same time 500 mg of P-4 is added. The reaction was carried out under shaking at 28° C. for 96 hours. TLC of the resulting reaction broth showed that P-4 had decreased in amount and, instead, PHO-4 had been produced.

EXAMPLE 15

*Streptomyces flavochromogenes* IFO 13443 was inoculated into a medium (pH 7.2) containing 1% dextrin, 1% glucose, 1% glycerol, 0.5% peptone, 0.5% yeast extract, 0.5% meat extract, 0.3% sodium chloride and 0.5% precipitated calcium carbonate, and cultivation was carried out under shaking at 28° C. for 18 hours. To 4 l of the resulting culture broth was added 200 mg of P-3 and the reaction was carried out under shaking at 28° C. for 72 hours. TLC of the above reaction broth showed that P-3 had decreased in amount and, instead, PHO-3 had been produced.

EXAMPLE 16

*Streptomyces olivaceiscleroticus* IFO 13484 was cultivated in the manner as Example 15 and 1 g of P-3 was added to 5 l of the resulting culture broth. The reaction was conducted under shaking at 28° C. for 72 hours to obtain a reaction broth. TLC of this reaction broth showed that P-3 had decreased in amount and, instead, PHO-3 had been produced.

EXAMPLE 17

*Streptomyces flaviscleroticus* IFO 13357 was cultivated in the manner as Example 15 and 1 g of P-3 is added to 5 l of the resulting culture broth. The reaction was carried out under shaking at 28° C. for 72 hours to obtain a reaction broth. TLC of this reaction broth showed that P-3 had decreased in amount and, instead, PHO-3 had been produced.

EXAMPLE 18

*Chainia nigra* IFO 13362 was cultivated in the manner as Example 15 and 1 g of P-3 was added to 5 l of the resulting culture broth. The reaction was conducted under shaking at 28° C. for 72 hours to obtain a reaction broth. TLC of this reaction broth showed that P-3 had decreased in amount and, instead, PHO-3 had been produced.

EXAMPLE 19

*Chainia nigra* IFO 13362 was cultivated in the manner as Example 15 and 1 g of P-0 was added to 5 l of the resulting culture broth. The reaction was conducted under shaking at 28° C. for 72 hours to obtain a reaction broth. TLC of this reaction broth showed that P-0 had decreased in amount and, instead, PHO-0 had been produced.

EXAMPLE 20

*Streptosporangium roseum* IFO 3776 was cultivated in the manner as Example 1 and 200 mg of P-3 was added to 4 l of the culture broth. The reaction was carried out under shaking at 28° C. for 72 hours to obtain a reaction broth. TLC of this reaction broth showed that P-3 had decreased in amount and, instead, PHO-3 had been produced.

EXAMPLE 21

In 10 ml of tetrahydrofuran were dissolved 300 mg of the PHO-3 crystals obtained in Example 13 and after cooling to −5° C., 300 mg of lithium aluminum hydride was added. The reaction mixture was transferred to an ice-water bath and stirred for 30 minutes. Then, 30 ml of ethyl acetate and 20 ml of 1/200 N HCl were added, followed by extraction with 200 ml of ethyl acetate. The ethyl acetate layer was washed with a saturated aqueous solution of sodium chloride, washed with water, dried over anhydrous sodium sulfate and concentrated under reduced pressure. The concentrate was applied to the top of a silica gel column (30 ml) and elution was carried out with ethyl acetate, ethyl acetate-methanol (20:1) and ethyl acetate-methanol (10:1) in that order. Each fraction was spotted on a silica gel plate (Kieselgel 60$F_{254}$, 0.25 mm, 20×20 cm) and developed with $H_2O$-saturated ethyl acetate. Then, detection was carried out by ultraviolet light and the fractions absorbing in the neighborhood of Rf 0.10 were collected and concentrated under reduced pressure. The concentrate was allowed to stand, whereupon crystals of PHO-0 were obtained (163 mg). The physico-chemical properties of this product were in agreement with those of PHO-0 according to Example 5.

EXAMPLE 22

In 2 ml of tetrahydrofuran were dissolved 20 mg of the epi-PHO-4 crystals obtained in Example 11 and after cooling to −5° C., 20 mg of lithium aluminum hydride was added. This reaction mixture was treated as in Example 21 and subjected to preparative TLC on silica gel. After development with $H_2O$-saturated ethyl acetate over a distance of 17 cm, the zone absorbing in the neighborhood of Rf 0.10 was scraped off, extracted with ethyl acetate containing a small amount of water, washed with water, dried over anhydrous sodium sulfate and concentrated under reduced pressure. This procedure provided epi-PHO-0 (8 mg), the physicochemical properties of which were in agreement with those of epi-PHO-0 according to Example 5.

EXAMPLE 23

PHO-3 (50 mg) was dissolved in 1 ml of pyridine, then 0.5 ml of acetic anhydride was added, and the mixture was allowed to stand at room temperature overnight. Methanol (1 ml) was added to the reaction mixture so as to cause decomposition of excess acetic anhydride. The resulting mixture was concentrated under reduced pressure and the concentrate was dissolved in 100 ml of ethyl acetate. The ethyl acetate solution was washed in sequence with diluted hydrochloric acid, aqueous sodium bicarbonate solution and water and then dried over $Na_2SO_4$, and the solvent was distilled off under reduced pressure. The residue was crystallized from a mixture of methylene chloride and diethyl ether to give 47 mg of PHO-3 15-acetate.
m.p. 253°–255° C.

UV spectrum $\lambda_{max}^{MeOH}$: 233 nm ($\epsilon$30,700), 253 nm ($\epsilon$27,200), 281 nm ($\epsilon$5450), 290 nm ($\epsilon$5450).

TLC (silica gel glass plate, Kieselgel 60$F_{254}$, 0.25 mm; developing solvent: water-saturated ethyl acetat): Rf: 0.41.

EXAMPLE 24

PHO-3 (50 mg) was dissolved in 1 ml of pyridine, then 0.5 ml of propionic anhydride was added, and the mixture was allowed to stand at room temperature overnight. The reaction mixture was treated by the procedure of Example 23.

Crystallization from a mixture of ethyl acetate and diethyl ether gave 47 mg of PHO-3 15-propionate. m.p. >270° C.

TLC (under the same conditions as in Example 23): Rf: 0.49.

EXAMPLE 25

PHO-3 (50 mg) was dissolved in 1 ml of pyridine, 0.5 ml of n-butyric anhydride was added, and the mixture was allowed to stand at room temperature overnight. The reaction mixture was treated by the procedure of Example 23 to give 46 mg of PHO-3 15-n-butyrate. m.p. 243° to 245° C.

TLC (under the same conditions as in Example 23): Rf: 0.53.

EXAMPLE 26

PHO-3 (50 mg) was dissolved in 1 ml of pyridine, 0.5 ml of n-valeric anhydride was added, and the mixture was allowed to stand at room temperature overnight. The reaction mixture was treated by the procedure of Example 23 to give 45 mg of PHO-3 15-n-valerate. m.p. 223° to 225° C.

TLC (under the same conditions as in Example 23): Rf: 0.54.

EXAMPLE 27

PHO-4 (30 mg) was dissolved in 1 ml of pyridine, 0.5 ml of acetic anhydride was added, and the mixture was allowed to stand at room temperature overnight. The reaction mixture was treated by the procedure of Example 23 to give 24 mg of PHO-4 15-acetate.

TLC (under the same conditions as in Example 23): Rf: 0.47.

EXAMPLE 28

PHO-2 (20 mg) was dissolved in 1 ml of pyridine, 0.5 ml of acetic acid was added, and the mixture was allowed to stand at room temperature overnight. The reaction mixture was treated by the procedure of Example 23 to give 16 mg of PHO-2 15-acetate.

TLC (under the same conditions as in Example 23): Rf: 0.36.

EXAMPLE 29

PHO-3 (50 mg) was dissolved in 1 ml of pyridine 50 mg of succinic anhydride was added, and the mixture was allowed to stand at room temperature overnight. To the liquid reaction mixture was added 100 ml of ethyl acetate, and the ethyl acetate solution was washed with diluted hydrochloric acid and then shaken with two 50 ml portions of 2% aqueous sodium bicarbonate solution so as to transfer the objective product to the aqueous layer. The aqueous layers were combined, adjusted to pH 3 with diluted hydrochloric acid and extracted two 50 ml portions of ethyl acetate. The ethyl acetate extracts were washed with water, dried and concentrated under reduced pressure to give 34 mg of PHO-3 15-succinate.

TLC (under the same conditions as in Example 23): Rf: 0.12.

EXAMPLE 30

PHO-3 (50 mg) was dissolved in 0.8 ml of pyridine, and the solution was cooled on an ice bath. Four (4) drops of acetic formic anhydride cooled in advance to 0° C. were added, and the mixture was stirred at 0° C. for 15 minutes. The liquid reaction mixture was concentrated under reduced pressure, 20 ml of petroleum ether was added to the concentrate, and the resulting precipitate was collected by filtration and crystallized from a mixture of ethyl acetate and diethyl ether to give 27 mg of PHO-3 15-formate.

m.p. 236° to 238° C.

TLC (under the same conditions as in Example 23): Rf: 0.42.

EXAMPLE 31

PHO-3 (50 mg) was dissolved in 20 ml of dried methylene chloride, 1 ml of pyridine was added, and the mixture was cooled on an ice bath. Four (4) drops of benzoyl chloride was added, and the mixture was stirred first at 0° C. for 10 minutes and then at room temperature for 2 hours. The liquid reaction mixture was washed in sequence with diluted hydrochloric acid, aqueous sodium bicarbonate solution and water, and dried. The solvent was evaporated to dryness under reduced pressure, and the residue was crystallized from ethyl acetate to give 49 mg of PHO-3 15-benzoate. m.p. >270° C.

TLC (under the same conditions as in Example 23): Rf: 0.55.

EXAMPLE 32

PHO-3 (35 mg) was dissolved in 2 ml of pyridine, 45 mg of monochloroacetic acid and 130 mg of dicyclohexylcarbodiimide were added, and the mixture was allowed to stand at room temperature overnight. Methanol (2 ml) was added to the liquid reaction mixture, the resulting mixture was concentrated under reduced pressure, and 50 ml of ethyl acetate was added to the residue. The insoluble matter was filtered off, and the ethyl acetate solution was washed in sequence with diluted hydrochloric acid, aqueous sodium bicarbonate solution and water, dried and evaporated to dryness under reduced pressure. The residue was crystallized from ethyl acetate to give 27 mg of PHO-3 15-monochloroacetate.

TLC (under the same conditions as in Example 23): Rf: 0.52.

EXAMPLE 33

PHO-3 (50 mg) was dissolved in 20 ml methylene chloride, then 50 mg of crotonic acid, 130 mg of dicyclohexylcarbodiimide and 50 mg of 4-dimethylaminopyridine were added, and the mixture was stirred at room temperature for an hour. The reaction mixture was washed in sequence with diluted hydrochloric acid, aqueous sodium bicarbonate solution and water, the solvent was evaporated to dryness under reduced pressure, ethyl acetate was added to the residue, the insoluble matters were filtered off, and the solvent was distilled off under reduced pressure to give 46 mg of PHO-3 15-crotonate.

m.p. 257° to 259° C.

TLC (under the same conditions as in Example 23): Rf: 0.48.

EXAMPLE 34

PHO-3 (40 mg) was dissolved in 2 ml of pyridine 0.5 ml of acrylic acid and 130 mg of dicyclohexylcarbodiimide were added, and the mixture was allowed to stand at room temperature overnight. Methanol (2 ml) was added to the liquid reaction mixture, the whole mixture was concentrated under reduced pressure, 50 ml of ethyl acetate was added to the residue, the insoluble matter was filtered off, and the mother liquor was concentrated under reduced pressure to give 33 mg of PHO-3 15-acrylate.

m.p. 240° to 242° C.

TLC (under the same conditions as in Example 23): Rf: 0.46.

EXAMPLE 35

PHO-3 (50 mg) was dissolved in 2 ml of pyridine, 60 mg of monoethyl succinate and 130 mg of dicyclohexylcarbodiimide were added, and the mixture was allowed to stand at room temperature overnight. The reaction mixture was treated by the procedure of Example 34 to give 37 mg of PHO-3 15-ethylsuccinate.

TLC (under the same conditions as in Example 23): Rf: 0.47.

EXAMPLE 36

In 20 ml of dried methylene chloride was dissolved 200 mg of PHO-3, followed by addition of 1 ml of pyridine. The mixture was cooled in an ice-bath. To the mixture thus obtained was added 0.5 ml of isobutyric chloride, and the mixture was stirred for 20 minutes. The reaction mixture was cooled in an ice-bath, and extracted with 50 ml of methylene chloride. The extract was washed with diluted hydrochloric acid, sodium bicarbonate, and water in that order and dried, followed by concentration under reduced pressure. The residue was subjected to recrystallization with a mixed solvent of ethyl acetate and diethyl ether, whereby 180 mg of crystals of PHO-3 15-isobutyrate was obtained.

m.p. 241°–243° C.

TLC (under the same conditions as in Example 23): Rf: 0.53.

EXAMPLE 37

In 30 ml of methylene chloride was dissolved 150 mg of PHO-3, followed by addition of 0.5 ml of isovaleric acid, 400 mg of dicyclohexylcarbodiimide, 1 ml of pyridine and 10 mg of 4-dimethylaminopyridine. The mixture was stirred at a room temperature for 2 hours. The reaction mixture was washed with diluted hydrochloric acid, sodium bicarbonate and water in that order and dried, followed by concentration under reduced pressure. To thus obtained residue was added 100 ml of ethyl acetate, and insoluble matters were removed by filtration. The mother liquor was concentrated, followed by addition of a small amount of diethyl ether to give 103 mg of PHO-3 15-isovalerate.

m.p. 208° to 210° C.

TLC (under the same conditions as in Example 23): Rf: 0.54

EXAMPLE 38

In 0.5 ml of pyridine was dissolved 50 mg PHO-0, followed by addition of 4 drops of n-valeric anhydride. The mixture was allowed to stand at room temperature for 6 hours. To the reaction mixture was added 30 ml of ethyl acetate. The ethyl acetate layer was recovered and washed with diluted hydrochloric acid, sodium bicarbonate and water in that order and dried, followed by concentration under reduced pressure. Thus obtained residue was subjected to recrystallization with a mixed solvent of ethyl acetate and diethyl ether, whereby 36 mg of PHO-0 15-n-valerate was obtained.

m.p. 187° to 189° C.

TLC (under the same conditions as in Example 23): Rf: 0.27

EXAMPLE 39

In 1 ml of pyridine was dissolved 33 mg of the epi-PHO-3 obtained in Example 3 followed by addition of 4 drops of acetic anhydride. The mixture was allowed to stand at room temperature overnight. Thereafter, the mixture was worked up in the manner as Example 23 to obtain crystals of epi-PHO-3 15-acetate (23 mg).

Mass spectrum: m/e 692 (M+); m/e 631, 571, 556, 536, 483, 468, 448.

TLC Rf=0.39 [under the same conditions as in Example 23].

What we claim is:

1. A maytansinoid compound of the formula:

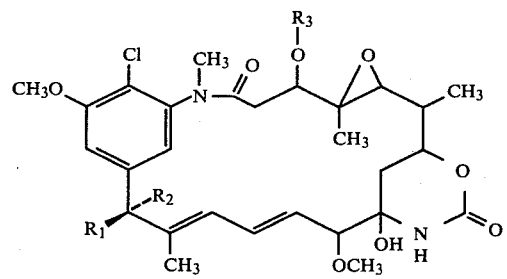

wherein
when $R_3$ designates hydrogen or alkanoyl containing not more than 5 carbon atoms except

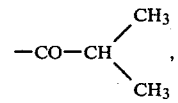

$R_1$ is hydroxyl and $R_2$ is hydrogen;

when $R_3$ designates hydrogen or alkanoyl containing not more than 5 carbon atoms, $R_1$ is hydrogen and $R_2$ is hydroxyl;

when $R_3$ designates hydrogen or alkanoyl of 2 to 5 carbon atoms other than

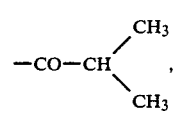

$R_2$ is hydrogen and $R_1$ is formyloxy, alkanoyloxy of 2 to 7 carbon atoms, alkenylcarbonyloxy of 3 to 5 carbon atoms or ArCOO, Ar being selected from the group consisting of phenyl, benzyl, cinnamyl, phenethyl and styryl, and wherein the said alkanoyloxy, alkenylcarbonyloxy or ArCOO may optionally be substituted by at most three substituents X and the radical Ar may be optionally substituted with 1 to 3 $C_{1-4}$-alkyl groups;

when $R_3$ designates

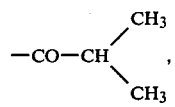

$R_2$ is hydrogen, and $R_1$ is formyloxy, acetoxy, alkanoyloxy of 3 to 7 carbon atoms, alkenylcarbonyloxy of 3 to 5 carbon atoms, or ArCOO, Ar being selected from the group consisting of phenyl, benzyl, cinnamyl, phenethyl and styryl, and wherein said alkanoyloxy, alkenylcarbonyloxy or ArCOO may optionally be substituted by at most three substituents X and the radical Ar may be optionally substituted with 1 to 3 $C_{1-4}$-alkyl groups;

and when $R_3$ designates hydrogen or alkanoyl containing not more than 5 carbon atoms, $R_1$ is hydrogen and $R_2$ is alkanoyloxy of 2 to 5 carbon atoms; wherein X is selected from the group consisting of $C_{1-4}$-alkoxy, $C_{2-4}$ alkanoyl, $C_{2-4}$ alkanoyloxy, $C_{2-4}$ alkoxycarbonyl, halogen, nitro, cyano, trifluoromethyl, di-$C_{1-4}$-alkylamino, $C_{1-4}$ alkylthio, methylsulfinyl, methylsulfonyl, oxo, thioxo, $C_{1-4}$ alkanoylamino and carboxyl.

2. A compound as claimed in claim 1, wherein $R_1$ is alkanoyloxy of 2 to 7 carbon atoms, alkenylcarbonyloxy of 3 to 5 carbon atoms or ArCOO, $R_2$ is hydrogen and $R_3$ is isovaleryl.

3. A compound as claimed in claim 1, when $R_1$ is alkanoyloxy of 3 to 7 carbon atoms, alkenylcarbonyloxy of 3 to 5 carbon atoms, ArCOO, chloroacetoxy, dichloroacetoxy or trichloroacetoxy, $R_2$ is hydrogen and $R_3$ is isobutyryl.

4. A compound as claimed in claim 1, wherein $R_1$ is hydrogen, $R_2$ is alkanoyloxy of 2 to 5 carbon atoms and $R_3$ is isobutyryl.

5. A compound as claimed in claim 1, wherein $R_1$ is hydroxyl, $R_2$ is hydrogen and $R_3$ is hydrogen.

6. A compound as claimed in claim 1, wherein $R_1$ is hydroxyl, $R_2$ is hydrogen and $R_3$ is acetyl.

7. A compound as claimed in claim 1, wherein $R_1$ is hydroxyl, $R_2$ is hydrogen and $R_3$ is propionyl.

8. A compound as claimed in claim 1, wherein $R_1$ is hydroxyl, $R_2$ is hydrogen and $R_3$ is isovaleryl.

9. A compound as claimed in claim 1, wherein $R_1$ is hydrogen, $R_2$ is hydroxyl and $R_3$ is isobutyryl.

10. A compound as claimed in claim 1, wherein $R_1$ is propionyloxy, $R_2$ is hydrogen and $R_3$ is isobutyryl.

11. A compound as claimed in claim 1, wherein $R_1$ is n-butyryloxy, $R_2$ is hydrogen and $R_3$ is isobutyryl.

12. A compound as claimed in claim 1, wherein $R_1$ is n-valeryloxy, $R_2$ is hydrogen and $R_3$ is isobutyryl.

13. A compound as claimed in claim 1, wherein $R_1$ is acetoxy, $R_2$ is hydrogen and $R_3$ is isovaleryl.

14. A compound as claimed in claim 1, wherein $R_1$ is benzoyloxy, $R_2$ is hydrogen and $R_3$ is isobutyryl.

15. A compound as claimed in claim 1, wherein $R_1$ is monochloroacetoxy, $R_2$ is hydrogen and $R_3$ is isobutyryl.

16. A compound as claimed in claim 1, wherein $R_1$ is crotonoyloxy, $R_2$ is hydrogen and $R_3$ is isobutyryl.

17. A compound as claimed in claim 1, wherein $R_1$ is acryloyloxy, $R_2$ is hydrogen and $R_3$ is isobutyryl.

18. A compound as claimed in claim 1, wherein $R_1$ is isobutyryloxy, $R_2$ is hydrogen and $R_3$ is isobutyryl.

19. A compound as claimed in claim 1, wherein $R_1$ is isovaleryloxy, $R_2$ is hydrogen and $R_3$ is isobutyryl.

20. A compound as claimed in claim 1, wherein $R_1$ is hydrogen, $R_2$ is acetoxy and $R_3$ is isobutyryl.

* * * * *